United States Patent
Timm et al.

(10) Patent No.: US 7,713,288 B2
(45) Date of Patent: May 11, 2010

(54) SPRING JUNCTION AND ASSEMBLY METHODS FOR SPINAL DEVICE

(75) Inventors: Jens P. Timm, West Haven, CT (US); Alvin Johnson, Suffield, CT (US)

(73) Assignee: Applied Spine Technologies, Inc., Rocky Hill, CT (US)

( * ) Notice: Subject to any disclaimer, the term of this patent is extended or adjusted under 35 U.S.C. 154(b) by 446 days.

(21) Appl. No.: 11/196,102

(22) Filed: Aug. 3, 2005

(65) Prior Publication Data

US 2007/0032123 A1    Feb. 8, 2007

(51) Int. Cl.
*A61B 17/70*    (2006.01)
(52) U.S. Cl. ...................................... 606/257
(58) Field of Classification Search .......... 267/166, 267/167, 170, 179; 606/57–59, 61; 623/17.13
See application file for complete search history.

(56) References Cited

U.S. PATENT DOCUMENTS

| | | | |
|---|---|---|---|
| 2,733,596 A | 2/1956 | Painter | |
| 4,328,960 A | 5/1982 | Handke et al. | |
| 4,352,514 A | 10/1982 | Orima | |
| 4,558,852 A | 12/1985 | Steiner et al. | |
| 4,650,167 A | 3/1987 | Steiner et al. | |
| 4,743,260 A | 5/1988 | Burton | |
| 4,759,769 A | 7/1988 | Hedman et al. | |
| 4,807,859 A * | 2/1989 | Bolthouse | 267/170 |
| 5,034,011 A | 7/1991 | Howland | |
| 5,174,551 A | 12/1992 | Mintgen | |
| 5,180,393 A | 1/1993 | Commarmond | |
| 5,291,901 A | 3/1994 | Graf | |
| 5,329,933 A | 7/1994 | Graf | |
| 5,375,823 A | 12/1994 | Navas | |

(Continued)

FOREIGN PATENT DOCUMENTS

AU    744241    7/1999

(Continued)

OTHER PUBLICATIONS

Panjabi, The Stabilizing System of the Spine, Part I. Function, Dysfunction, Adaptation, and Enhancement, Journal of Spinal Disorders, 1992, vol. 5, No. 4, pp. 383-389.

(Continued)

*Primary Examiner*—Eduardo C Robert
*Assistant Examiner*—Elana B Fisher
(74) *Attorney, Agent, or Firm*—McCarter & English, LLP

(57) ABSTRACT

Spinal stabilization devices, systems and methods are provided that include a spring junction wherein a structural member is mountable to a spine attachment fastener and a resilient element is affixed to the structural member along an attachment region of the resilient element. The attachment region is disposed physically separately with respect to an active region of the resilient element. The attachment region can include a weld region produced via an E-beam welding process involving temperatures of 1000° F. or greater, wherein a heat-affected zone adjacent the weld region is disposed physically separately with respect to the active region. The resilient element may be a coil spring including bend regions adjacent its outermost (i.e., last) coils wherein the material of the coil spring initially bends away from the last coil, then bends back toward the last coil before terminating near the last coil.

19 Claims, 11 Drawing Sheets

U.S. PATENT DOCUMENTS

| | | |
|---|---|---|
| 5,415,661 A | 5/1995 | Holmes |
| 5,423,816 A | 6/1995 | Lin |
| 5,480,401 A | 1/1996 | Navas |
| 5,501,684 A | 3/1996 | Schlapfer et al. |
| 5,505,118 A | 4/1996 | Arnesen et al. |
| 5,540,688 A | 7/1996 | Navas |
| 5,562,737 A | 10/1996 | Graf |
| 5,653,680 A | 8/1997 | Cruz |
| 5,672,175 A | 9/1997 | Martin |
| RE36,221 E | 6/1999 | Breard et al. |
| 5,928,284 A * | 7/1999 | Mehdizadeh ............ 623/17.13 |
| 5,961,516 A | 10/1999 | Graf |
| 6,162,223 A | 12/2000 | Orsak et al. |
| 6,176,860 B1 | 1/2001 | Howard |
| 6,241,730 B1 | 6/2001 | Alby |
| 6,267,764 B1 | 7/2001 | Elberg |
| 6,293,949 B1 | 9/2001 | Justis et al. |
| 6,371,465 B1 | 4/2002 | Willis et al. |
| 6,375,681 B1 | 4/2002 | Truscott |
| 6,402,750 B1 * | 6/2002 | Atkinson et al. ............. 606/61 |
| 6,419,706 B1 | 7/2002 | Graf |
| 6,440,169 B1 | 8/2002 | Elberg et al. |
| 6,508,818 B2 | 1/2003 | Steiner et al. |
| 6,554,831 B1 | 4/2003 | Rivard et al. |
| 6,645,207 B2 | 11/2003 | Dixon et al. |
| 6,761,719 B2 | 7/2004 | Justis et al. |
| 6,835,205 B2 | 12/2004 | Atkinson et al. |
| 2002/0095154 A1 | 7/2002 | Atkinson et al. |
| 2002/0151978 A1 | 10/2002 | Zacouto et al. |
| 2003/0055427 A1 | 3/2003 | Fraf |
| 2003/0078667 A1 | 4/2003 | Manasas et al. |
| 2003/0171749 A1 | 9/2003 | Le Couedic et al. |
| 2003/0220642 A1 | 11/2003 | Freudiger |
| 2003/0220643 A1 | 11/2003 | Ferree |
| 2004/0049189 A1 | 3/2004 | Le Couedic et al. |
| 2004/0049190 A1 | 3/2004 | Biedermann et al. |
| 2004/0082954 A1 | 4/2004 | Teitelbaum et al. |
| 2004/0143264 A1 | 7/2004 | McAfee |
| 2004/0147928 A1 | 7/2004 | Landry et al. |
| 2004/0167523 A1 | 8/2004 | Jackson |
| 2006/0036240 A1 | 2/2006 | Colleran et al. ............. 606/61 |
| 2006/0064090 A1 | 3/2006 | Park ............ 606/61 |
| 2006/0189985 A1 * | 8/2006 | Lewis ............ 606/61 |

FOREIGN PATENT DOCUMENTS

| | | |
|---|---|---|
| CA | 2135838 | 5/1995 |
| CA | 2213058 | 2/1998 |
| EP | 0516567 | 12/1992 |
| EP | 0534874 | 3/1993 |
| EP | 0576379 | 12/1993 |
| EP | 0611554 | 8/1994 |
| EP | 0821917 | 2/1998 |
| EP | 1039855 | 6/2004 |
| FR | 2676911 | 12/1992 |
| FR | 2681520 | 3/1993 |
| FR | 2692468 | 12/1993 |
| FR | 2694182 | 2/1994 |
| FR | 2701650 | 8/1994 |
| FR | 2701651 | 8/1994 |
| FR | 2751864 | 2/1998 |
| FR | 2772594 | 6/1999 |
| FR | 2775891 | 9/1999 |
| FR | 2794362 | 12/2000 |
| FR | 2799949 | 4/2001 |
| FR | 2801782 | 6/2001 |
| FR | 2803188 | 7/2001 |
| FR | 2809304 | 11/2001 |
| FR | 2810873 | 1/2002 |
| FR | 2812535 | 2/2002 |
| GB | 2382304 | 5/2003 |
| JP | 6-285100 | 10/1994 |
| JP | 7-289562 | 11/1995 |
| JP | 10-71157 | 3/1998 |
| JP | 10-277070 | 10/1998 |
| WO | 99/32054 | 7/1999 |
| WO | 01/39678 | 6/2001 |
| WO | 01/45576 | 6/2001 |
| WO | 01/49192 | 7/2001 |
| WO | 02/00124 | 1/2002 |
| WO | 02/102259 | 12/2002 |

OTHER PUBLICATIONS

Panjabi, The Stabilizing System of the Spine, Part II. Neutral Zone and Instability Hypothesis, Journal of Spinal Disorders, 1992, vol. 5, No. 4, pp. 390-397.

PCT International Search Report dated Aug. 20, 2007.

* cited by examiner

SPRING JUNCTION AND ASSEMBLY METHODS FOR SPINAL DEVICE

BACKGROUND

1. Technical Field

The present disclosure relates to advantageous devices, systems and methods for spinal stabilization. More particularly, the present disclosure relates to devices, systems and methods for providing dynamic stabilization to the spine with systems/devices that include one or more enhanced spring junctions so as to provide clinically efficacious results.

2. Background Art

Each year, over 200,000 patients undergo lumbar fusion surgery in the United States. While fusion is effective about seventy percent of the time, there are consequences even to these successful procedures, including a reduced range of motion and an increased load transfer to adjacent levels of the spine, which may accelerate degeneration at those levels. Further, a significant number of back-pain patients, estimated to exceed seven million in the U.S., simply endure chronic low-back pain, rather than risk procedures that may not be appropriate or effective in alleviating their symptoms.

New treatment modalities, collectively called motion preservation devices, are currently being developed to address these limitations. Some promising therapies are in the form of nucleus, disc or facet replacements. Other motion preservation devices provide dynamic internal stabilization of the injured and/or degenerated spine, e.g., the Dynesys stabilization system (Zimmer, Inc.; Warsaw, IN) and the Graf Ligament. A major goal of this concept is the stabilization of the spine to prevent pain while preserving near normal spinal function.

To provide dynamic internal spinal stabilization, motion preservation devices may advantageously include dynamic junctions that exhibit multiple degrees of freedom and commonly include active force-absorbing/force-generating structures. Such structures may include one or more resilient elements, e.g., torsion springs and/or coil springs, designed and deployed so as to contribute strength and flexibility to the overall device. While the flexibility afforded by such resilient elements is plainly critical to the effectiveness of the respective devices of which they form a part, the elevated force levels associated with the use of such resilient elements can result in such resilient elements developing significant levels of internal stress. Depending on the magnitude and location thereof, internal stresses may pose the potential for stress-induced fatigue, material deformation and/or cracks. The FDA has promulgated rules (e.g., Title 21, Subchapter H, Part 888, Subpart D, Section 888.3070 regarding pedicle screw spinal systems) that, in relevant part, require manufacturers to demonstrate compliance with special controls, including but not limited to applicable mechanical testing standards geared toward high reliability and durability.

With the foregoing in mind, those skilled in the art will understand that a need exists for devices, systems and methods for motion-preserving spinal stabilization devices and systems having reliable, durable constructions. In addition, a need exists for manufacturing processes and/or techniques that may be used to reliably and efficiently produce motion-preserving spinal stabilization devices and systems. These and other needs are satisfied by the disclosed devices and systems that include advantageous spring junctions, as well as the associate methods for manufacture/assembly thereof.

SUMMARY OF THE PRESENT DISCLOSURE

According to the present disclosure, advantageous devices, systems and methods for spinal stabilization are provided. According to exemplary embodiments of the present disclosure, the disclosed devices, systems and methods include a spring junction that promotes reliable and efficacious spinal stabilization. The disclosed spring junction includes a structural member that is mounted or mountable with respect to a spine attachment fastener such as a pedicle screw, and a resilient element affixed to the structural member. The resilient element has an attachment region, along which the resilient element is affixed to the structural member, and an active region. The attachment region of the resilient element is physically separately disposed with respect to the active region thereof.

According to exemplary embodiments of the present disclosure, the spring junction includes a weld region. A heat-affected zone of the resilient element and associated with the weld region is disposed adjacent the weld region, but is physically separately disposed with respect to the active region of the resilient element. The active region of the resilient element is generally subjected to cyclical stress, e.g., during in situ use of the disclosed spinal stabilization device. In exemplary embodiments, the weld region is produced via a welding process, such as electron-beam welding, and accordingly may be subjected to welding temperatures of about 1000° F. or higher. In addition, in exemplary embodiments of the present disclosure, the resilient element takes the form of a spring, e.g., a coil spring or helical spring, which extends into the weld region and which is mounted with respect to the structural member to form the spring junction.

According to further exemplary embodiments of the present disclosure, the resilient element includes a bend region disposed between the weld region and an adjacent coil of the resilient element that extends along a helically-shaped path. The bend region is sized and shaped so as to initially bend away from the helically-shaped path before bending back toward the helically-shaped path and terminating at or in the weld region. In some such embodiments, the direction of the initial bend away from the helically-shaped path includes an axial component, but does not include a radial component. The bend region may further be sized and shaped so as to remain substantially peripherally aligned with such helically-shaped path when viewed in an axial direction with respect to the helically-shaped path. Of note, such spring junctions may be formed at opposite ends of the resilient element such that the resilient element/spring is mounted between spaced-apart structural members that are permitted to move relative to each other.

According to further exemplary embodiments of the present disclosure, a rod is mounted with respect to (or integrally formed with) the structural member. The rod may be advantageously adapted to mount with respect to an upwardly-extending structure associated with a pedicle screw. The rod/pedicle screw may be mounted with respect to each other such that relative movement of the rod relative to the pedicle screw is permitted in at least one plane.

In a still further embodiment, a method is disclosed for producing a spring junction in which a resilient element is welded to a structural member such that an active region of the resilient element is disposed physically separately with respect to the heat-affected zone associated with such welding. In some such embodiments, a further step is disclosed in which a resilient element is provided that defines an active region and a bend region, and wherein such welding results in the bend region being disposed between the active region and the heat-affected zone. Such a resilient element can include a coil extending along a helically-shaped path, and in which the bend region is configured so as to initially bend away from such helical path defined before bending back toward such helical path.

In a still further embodiment, a combination is provided that includes a structural member having a first end, a second end opposite the first end, an aperture between the first end and the second end, and a notch formed in the second end. The combination also includes a resilient element having a bend region at an end thereof, the bend region terminating at a termination. The resilient element is secured to the first end of the structural member such that the bend region extends through the aperture and the termination is lodged in the notch. In some such embodiments, the resilient element is further affixed to the structural member via a weld formed with respect to the termination and the structural member at the notch. In other such embodiments, the termination is configured and dimensioned so as to extend at least partially in the direction of the first end of the structural member, and the bend region is configured and dimensioned such that the termination can be threaded through the aperture, and thereby rotated toward and into the notch. In some such cases the structural member includes a helical groove formed in the first end and terminating adjacent the aperture, and the resilient element includes an active region adjacent the bend region and spaced apart from the termination, and the active region includes a coil threaded along the helical groove to an extent of the aperture.

The spring junction(s) of the present disclosure are typically employed as part of a spinal stabilization system that may advantageously include one or more of the following structural and/or functional attributes:

Exemplary embodiments of the spring junction (and associated spring/structural member subassembly) are capable of undergoing at least approximately 10,000,000 cycles of combined extension/contraction and bending (e.g., during mechanical testing);

Implementation of the disclosed spring junctions have no substantial effect on the footprint of the dynamic stabilization devices in which they are incorporated, e.g., the resilient elements (e.g., springs) of such spinal stabilization devices do not extend radially inwardly or outwardly to a greater extent than the dynamic stabilization devices that do not include the disclosed spring junctions, thereby preserving compatibility with existing components and/or proven or preferred geometries;

An outwardly/upwardly, then inwardly/downwardly extending bend region at each end of the resilient element, combined with a notch on the external end of each spring cap plate provides a snap-fit system which positively locates the ends of the resilient element within their respective notches during pre-welding assembly, and presents a convenient face for purposes of electronic-beam welding without undue risk of annealing and/or other types of damage to the active region of the resilient element.

Advantageous spine stabilization devices, systems and methods may incorporate one or more of the foregoing structural and/or functional attributes. Thus, it is contemplated that a system, device and/or method may utilize only one of the advantageous structures/functions set forth above, a plurality of the advantageous structures/functions described herein, or all of the foregoing structures/functions, without departing from the spirit or scope of the present disclosure. Stated differently, each of the structures and functions described herein is believed to offer benefits, e.g., clinical advantages to clinicians and/or patients, whether used alone or in combination with others of the disclosed structures/functions.

Additional advantageous features and functions associated with the devices, systems and methods of the present disclosure will be apparent to persons skilled in the art from the detailed description which follows, particularly when read in conjunction with the figures appended hereto. Such additional features and functions, including the structural and mechanistic characteristics associated therewith, are expressly encompassed within the scope of the present invention.

BRIEF DESCRIPTION OF THE DRAWINGS

To assist those of ordinary skill in the art in making and using the disclosed devices, systems and methods for achieving enhanced reliability, dependability, and/or durability, e.g., in a dynamic spinal stabilization device, reference is made to the appended figures wherein.

DESCRIPTION OF EXEMPLARY EMBODIMENTS

The present disclosure provides advantageous devices, systems and methods for improving the reliability, dependability and/or durability of spinal stabilization systems. More particularly, the present disclosure provides advantageous devices, systems and methods for mechanically mounting resilient elements (e.g., torsion springs and/or coil springs) to, and/or for coupling resilient elements between, structural members (e.g., plates, caps, flanges, rods, and/or bars) associated with dynamic spinal stabilization systems. The mounting and/or coupling methods/techniques of the present disclosure provide enhanced reliability, dependability and/or durability without significantly increasing material weight or volume requirements and without compromising the important functions of the dynamic spinal stabilization devices/systems of which they form a part.

The exemplary embodiments disclosed herein are illustrative of the advantageous spinal stabilization devices/systems and surgical implants of the present disclosure, and of methods/techniques for implementation thereof. It should be understood, however, that the disclosed embodiments are merely exemplary of the present invention, which may be embodied in various forms. Therefore, the details disclosed herein with reference to exemplary dynamic spinal stabilization systems and associated methods/techniques of assembly and use are not to be interpreted as limiting, but merely as the basis for teaching one skilled in the art how to make and use the advantageous dynamic spinal stabilization systems and alternative surgical implants of the present disclosure.

Figure 1:
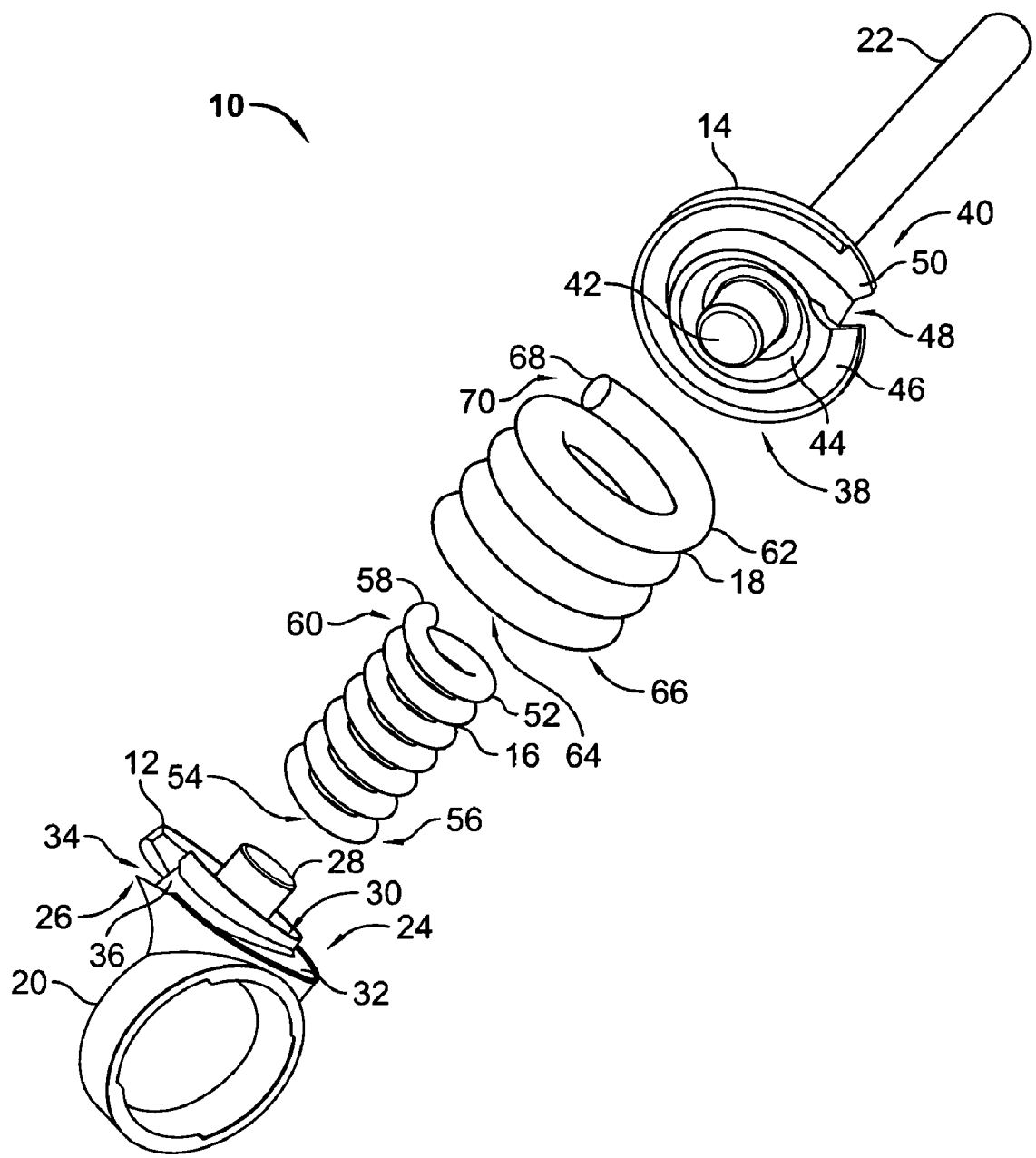
FIG. 1 is a perspective exploded assembly view of a spinal stabilization device/system, according to the present disclosure.

With reference to FIG. 1, components of a dynamic stabilization element 10 disclosed in commonly assigned U.S. Non-Provisional Patent Application Ser. No. 11/027,270, filed Dec. 31, 2004 (hereinafter "the '270 Application"), are shown in an exploded view. The disclosure of the '270 Application is hereby incorporated herein by reference in its entirety. As shown in FIG. 1, the dynamic stabilization element 10 includes two structural elements in the form of a spring cap 12 and a spring cap 14, and two resilient elements in the form of an inner spring 16 and an outer spring 18. The spring cap 12 is affixed to an attachment member 20 that is configured to be coupled to the head of a pedicle screw (not shown) via a dynamic joint (not shown). The spring cap 14 is affixed to a rod 22 that is configured to be attached to another attachment member (not shown) that is in turn coupled to the head of another pedicle screw (not shown) via another dynamic joint (not shown). The dynamic stabilization element 10 permits relative axial/longitudinal motion, as well as angular/rotational motion, of the rod 20 relative to the attachment member 20, as part of a larger spinal stabilization system (shown only in relevant part).

The spring cap 12 includes an interior end 24, an exterior end 26 opposite the interior end, a post 28 axially positioned on the interior end 24, an annular channel 30 formed in the interior end 24 around the post 28, a helically-shaped groove 32 formed in the interior end 24 around the annular channel 30, and an aperture 34 passing through the spring cap 12 between the interior and exterior ends 24, 26 thereof at an end 36 of the helically-shaped groove 32. The spring cap 14 includes an interior end 38, an exterior end 40 opposite the interior end 38, a post 42 axially positioned on the interior end 38 around the post 42, a helically-shaped groove 46 formed in the interior end 38 around the annular channel 44, and an aperture 48 passing through the spring cap 14 between the interior and exterior ends 38, 40 thereof at an end 50 of the helically-shaped groove 46.

The inner spring 16 consists of coils 52 sharing a common diameter and arranged sequentially about a common axis between a coil termination 54 (obscured) at an end 56 of the inner spring 16 and a coil termination 58 at another end 60 thereof opposite the end 56. The outer spring 18 consists of coils 62 sharing a common diameter and arranged sequentially about a common axis between a coil termination 64 (obscured) at an end 66 of the outer spring 18 and a coil termination 68 at another end 70 thereof opposite the end 66.

In the assembled state of the dynamic stabilization element 10, the inner spring 16 is positioned within the outer spring 18. The coil 52 at the end 56 of the inner spring 16 is positioned on or around the post 28 of the spring cap 12, and against the interior end 24 of the spring cap 12 so as to occupy (at least in part) the annular channel 30 formed therein. The coil 52 at the end 60 of the inner spring 16 is positioned on or around the post 42 of the spring cap 14 and against the interior end 38 of the spring cap 14 so as to occupy (at least in part) the annular channel 44 formed therein. In this way, the inner spring 16 is effectively captured between the spring cap 12 and the spring cap 14 and effectively floats relative to the opposing posts 28, 42. The coil 62 at the end 66 of the outer spring 18 is threaded into the interior end 24 of the spring cap 12 along the helically-shaped groove 32 at least until the coil termination 64 reaches the aperture 34 of the spring cap 12. The outer spring 18 is fixed with respect to the spring cap 12, e.g., by welding, and may be trimmed so as to be flush relative to an edge formed at the interface between the aperture 34 and the exterior end 26 of the spring cap 12. The coil 62 at the end 70 of the outer spring 18 is threaded into the interior end 38 of the spring cap 14 along the helically-shaped groove 46 at least until the coil termination 68 reaches the aperture 48 of the spring cap 14. The outer spring 18 is fixed with respect to the spring cap 14, e.g., by welding, and may be trimmed so as to be flush relative to an edge formed at the interface between the aperture 48 and the exterior end 40 of the spring cap 14.

As described in the '270 Application, the outer spring 18 is typically shorter than the inner spring 16, such that as the spring cap 12 and the spring cap 14 are brought toward each other (i.e., to permit the outer spring 18 to be mounted on both), the inner spring 16 is placed in compression. The degree to which the inner spring 16 is compressed is generally dependent on the difference in length as between the inner and outer springs 16, 18. Thus, the preload compression of the inner spring 16 may be controlled and/or adjusted in part through selection of the relative lengths of the inner and outer springs 16, 18. In addition to the preload compression of the inner spring 16, the mounting of the outer spring 18 with respect to the spring caps 12, 14 includes placing the outer spring 18 in tension. The overall preload of the dynamic stabilization element 10 corresponds to equal and opposite forces experienced by and/or contained within the inner and outer springs 16, 18.

The inner spring 16 reaches its free length (i.e., non compressed state) at or about the point at which a patient's movement exceeds a "neutral zone" (as described more completely in the '270 Application). Beyond this point, the inner spring 16 is free floating (e.g., on the opposing posts 28, 42), while the outer spring 18, already in tension, extends in length even further.

In the overall design of the disclosed spinal stabilization system, optimization of the attachment between the outer spring 18 and the spring cap 14 is desirable. In experimental studies associated with spinal stabilization devices of the type disclosed herein, it has been noted that direct welding of the outer spring 18 and the spring cap 14 may not provide an optimal means of attachment. While not intending to be bound by theory, it is believed that a "heat-affected" zone may be created in the coil 62 at the end 70 of the outer spring 18 as a result of the process of welding the outer spring 18 to the spring cap 14. More particularly, such heat-affected zone is believed to arise as a result of an annealing effect brought about by the migration of excess heat arising from an electronic-beam welding process. In accordance with such electronic beam or E-beam welding processes, elevated temperatures in a range of approximately 1000° F. or higher are used to affix the outer spring 18 to the spring cap 14 by essentially melting such components together. The heat-affected zone so produced can be at least 0.005"-0.030" in axial length, and is located immediately adjacent the weld formed at the end 70 of the outer spring 18, and along the active region of the outer spring 18. (As used herein in reference to a spring or resilient element, the term "active region" or "active portion" refers to a region, portion, or part of the spring or resilient element which, during normal in-situ use and/or representative mechanical testing of the spring or resilient element, actively contributes to the characteristic stiffness of the spring or resilient element, and/or actively participates in the axial travel and/or lateral bending thereof.) The heat-affected zone can include a soft or weak point on the coil 62 at which a Rockwell hardness of the material of the outer spring 18, ordinarily falling within a range of from approximately 46 to approximately 54, dips sharply; e.g., to a value in a range of from approximately 20 to approximately 24.

According to the present disclosure, geometric/structural modifications to the outer spring 18 and the spring cap 14 have been found to advantageously enhance the reliability and durability of dynamic stabilization element 10. Exemplary embodiments of the advantageous geometric/structural modifications to the outer spring 18 and the spring cap 14 are described hereinbelow with reference to FIGS. 2-14, as is a beneficial cooling/supercooling step involving the modified outer spring and the modified spring caps associated therewith. As a result of these geometric/structural modifications, and/or of the cooling/supercooling step, a durability standard of 10,000,000+ failure-free cycles has been achieved with apparatus in which an outer spring has been welded to its associated spring caps to form a dynamic stabilization device as described herein.

According to exemplary embodiments of the present disclosure, the geometric/structural modifications include the creation of a substantial physical separation of the active portion of the outer spring from the heat-affected zone associated with the E-beam welding process, and/or from the actual site of the weld formed between the attached components. As a result of this separation, to the extent that any region of the outer spring becomes significantly annealed, and/or is brought to a significantly lowered Rockwell hardness value as a result of E-beam welding, the amount of cyclic stress to which that softened or annealed portion is exposed is substantially reduced and/or brought to such a low level that the respective junctions between the outer spring and its associated spring caps can exhibit very high levels of reliability/durability.

Figure 2:
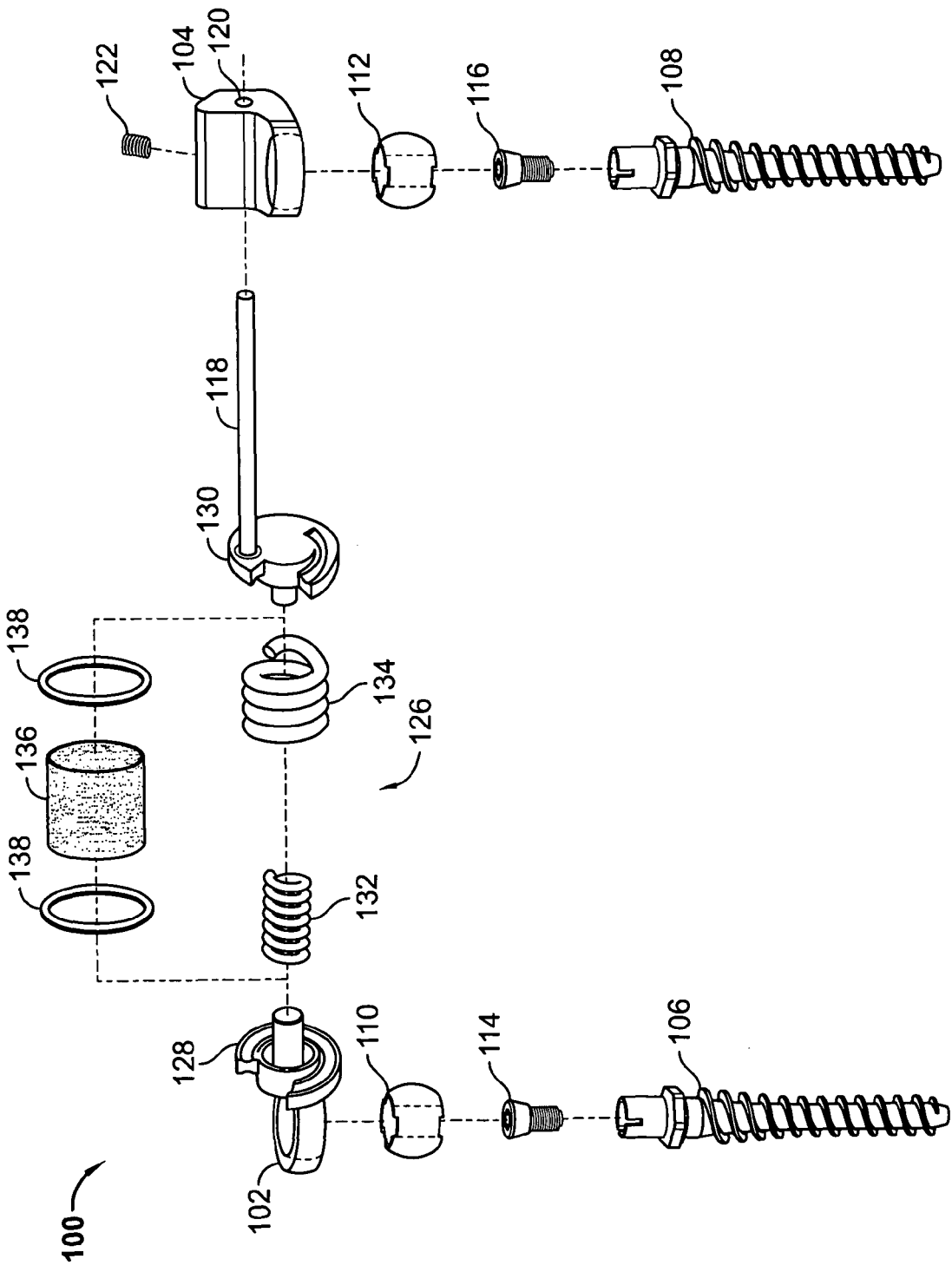
FIG. 2 is an exploded assembly view of a spinal stabilization device/system, including pedicle screws and associated mounting structures, in accordance with an embodiment of the present disclosure.
Figure 3:
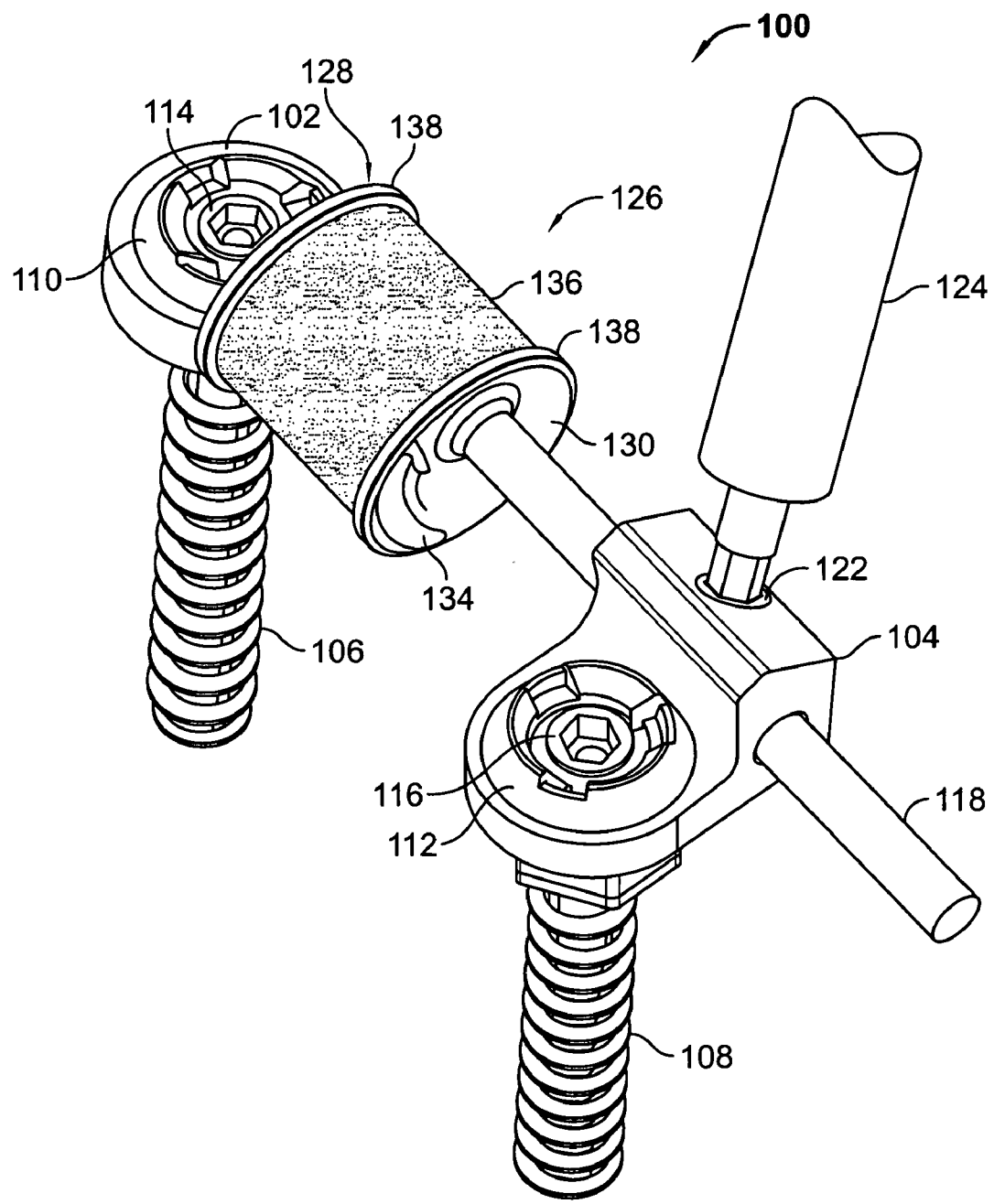
FIG. 3 is an unexploded assembly view of the exemplary spinal stabilization device/system of FIG. 2.

With reference to FIGS. 2 and 3, a dynamic spinal stabilization system 100 is shown in accordance with an exemplary embodiment of the present disclosure. Referring to FIG. 2, the spinal stabilization system 100 includes attachment members 102, 104, pedicle screws 106, 108, ball/spherical elements 110, 112, and set screws 114, 116. The attachment member 102 is configured to receive the ball/spherical element 110. The ball/spherical element 110 then receives the head of the pedicle screw 106 such that a global/dynamic joint is formed between the attachment member 102 and the head of the pedicle screw 106 (see also FIG. 3). The set screw 114 is then inserted into the head of the pedicle screw 106 (see also FIG. 3), thereby securing the head of the pedicle screw 106 within the baluspherical element 110. The attachment member 104 is configured to receive the ball/spherical element 112. The ball/spherical element 112 then receives the head of the pedicle screw 108 such that a global/dynamic joint is formed between the attachment member 104 and the head of the pedicle screw 108 (see also FIG. 3). The set screw 116 is then inserted into the head of the pedicle screw 108 (see also FIG. 3), thereby securing the head of the pedicle screw 108 within the ball/spherical element 112.

The spinal stabilization system 100 also includes a rod 118. The rod is configured to be inserted into the attachment member 104, which includes a transverse aperture 120 to accommodate the rod 118, and a set screw 122 to secure the rod 118 at a desired position within the transverse aperture 120 (see also FIG. 3, in which a hex driver 124 is shown turning the set screw 122 against the rod 118).

The spinal stabilization system 100 further includes a dynamic stabilization element 126 between the rod 118 and the attachment member 102. The dynamic stabilization element 126 includes structural members 128, 130, an inner resilient element 132, an outer resilient element 134, a sheath member 136, and two end clamps 138. As shown in FIG. 3, the inner resilient element 132 (obscured) and outer resilient element 134 (partially obscured) are positioned within the sheath member 136, and an end clamp 138 secures the sheath member 136 to each of the structural members 128, 130. This prevents undesirable interaction or interference between the inner and outer resilient elements 132, 134 and anatomical structures in situ. Referring again to FIG. 2, the inner resilient element 132 is constructed and functions in manners substantially similar to those of the inner spring 16 described hereinabove with reference to the dynamic stabilization element 10. The inner resilient element 132 is also deployed and employed in the dynamic stabilization element 126 in manners substantially similar to those in which the inner spring 16 is deployed and employed in the dynamic stabilization element 10 described hereinabove.

The following components of the dynamic stabilization element 126 will now be described in greater detail: the structural member 128 (with reference to FIGS. 4-6), the structural member 130 (with reference to FIGS. 7-9), and the outer resilient element 134 (with reference to FIG. 10). Next, the manner in which the structural members 128, 130 and the outer resilient element 134 are assembled will be discussed (with particular reference to FIGS. 11-14). Then, the functions of the dynamic stabilization element 126 will be discussed, followed by a discussion of the characteristic advantages of the dynamic stabilization element 126.

Figure 4:
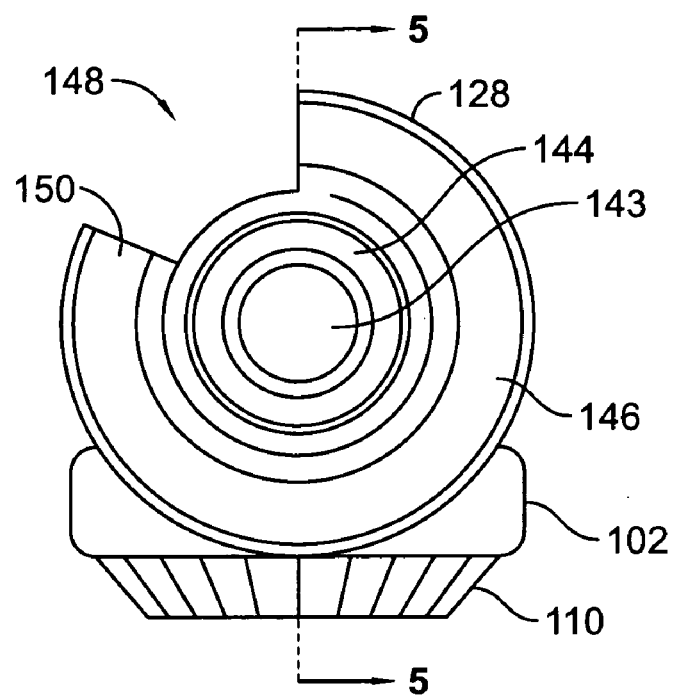
FIGS. 4, 5 and 6 are interior end, exterior end, and cross-sectional views of a structural member associated with the exemplary spinal stabilization device/system of FIGS. 2-3.
Figure 5:
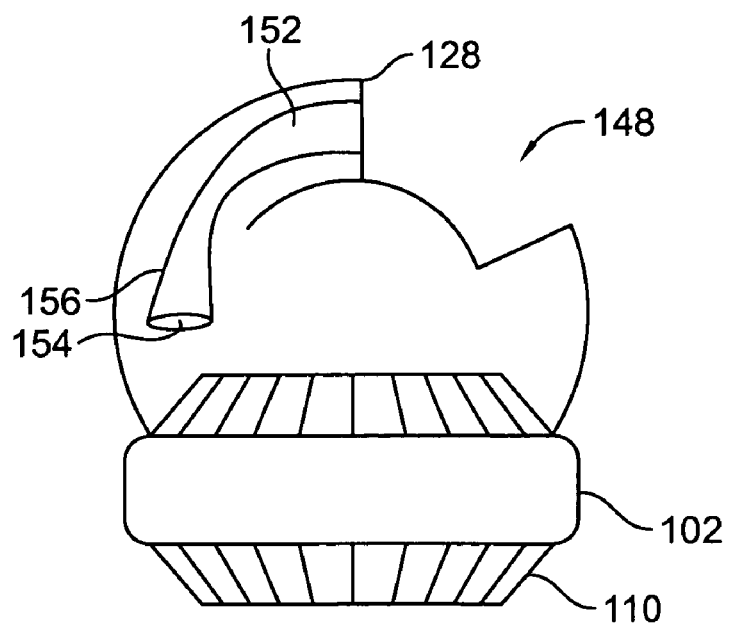
Figure 6:
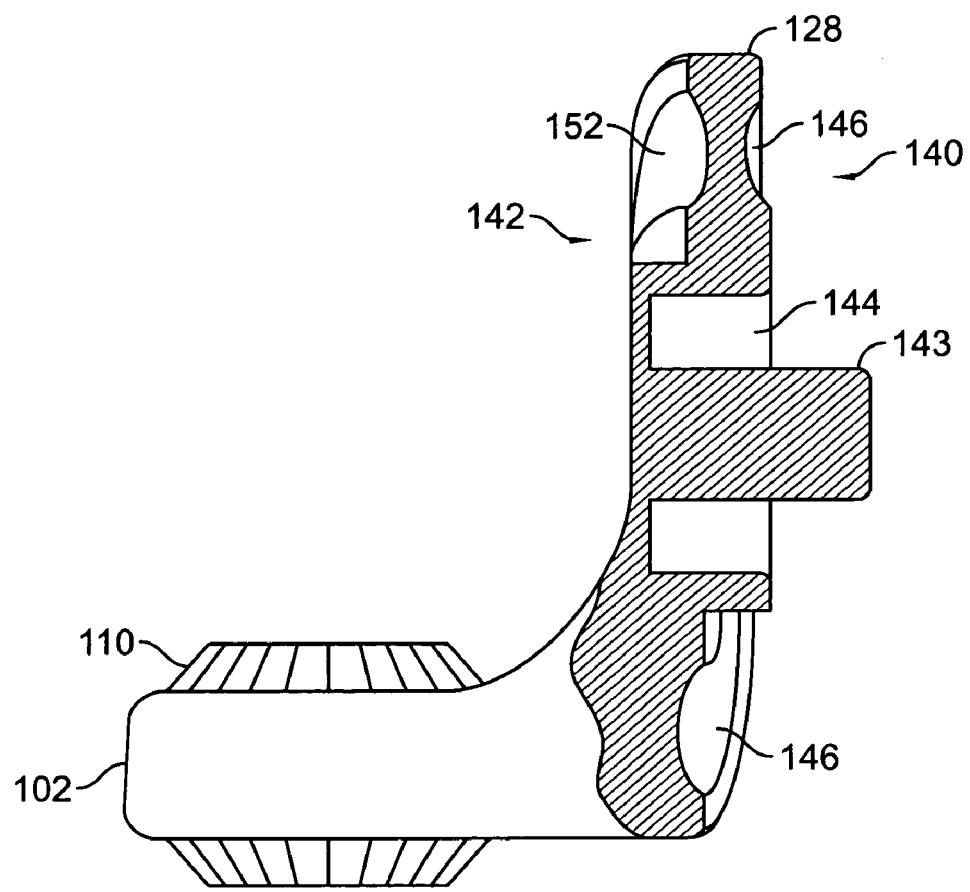

Referring now to FIGS. 4-6, the structural member 128 is affixed to (e.g., is of unitary construction with) the attachment member 102 (the ball/spherical element 110 is also shown within the attachment member 102) and takes the form of a plate having multiple features permitting the structural member 128 to fiction in the manner of an end cap or spring cap with respect to the inner and outer resilient elements 132, 134 (FIG. 2). The structural member 128 includes an interior end 140, an exterior end 142 opposite the interior end 140, a post 143 axially positioned on the interior end 140, an annular channel 144 formed in the interior end 140 around the post 143, a helically-shaped groove 146 formed in the interior end 140 around the annular channel 144, an aperture 148 passing through the structural member 128 between the interior and exterior ends 140, 142 thereof at an end 150 of the helically-shaped groove 146, a short groove 152 formed in the exterior end 142 adjacent the aperture 148, and a notch 154 formed in the exterior end 142 at an end 156 of the short groove 152. The structure and function of the structural member 128 will be described in greater detail hereinafter.

Figure 7:
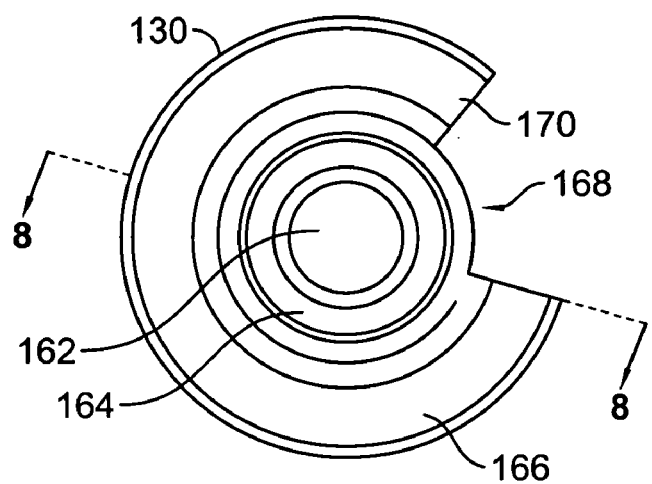
FIGS. 7, 8 and 9 are interior end, exterior end, and cross sectional views of another structural member associated with exemplary spinal stabilization device/system of FIGS. 2-3.
Figure 8:
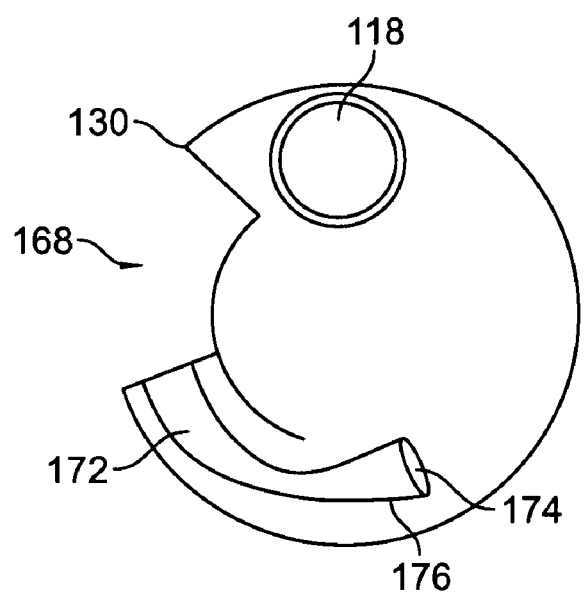
Figure 9:
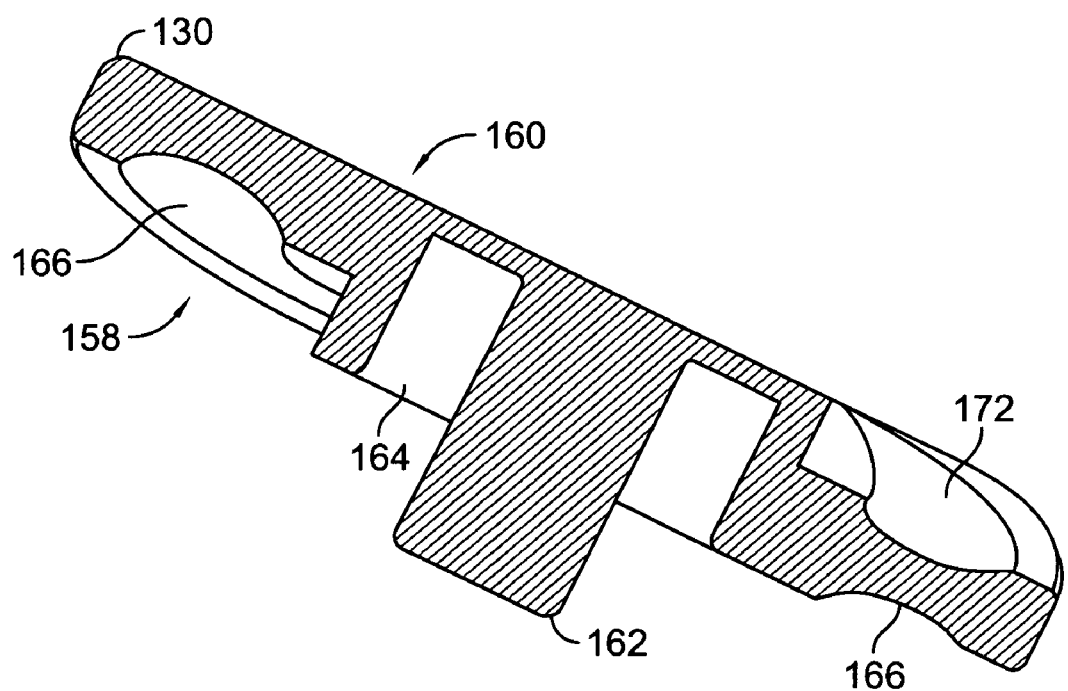

Referring now to FIGS. 7-9, the structural member 130 is affixed to (e.g., is of unitary construction with) the rod 118 (which is positioned off-axis or off-center with respect to the structural member 130), and takes the form of a plate having multiple features permitting the structural member 130 to function in the manner of an end cap or spring cap with respect to the inner and outer resilient elements 132, 134 (FIG. 2). The structural member 130 includes an interior end 158, an exterior end 160 opposite the interior end 158, a post 162 axially positioned on the interior end 158, an annular channel 164 formed in the interior end 158 around the post 162, a helically-shaped groove 166 formed in the interior end 158 around the annular channel 164, an aperture 168 passing through the structural member 130 between the interior and exterior ends 158, 160 thereof at an end 170 of the helically-shaped groove 166, a short groove 172 formed in the exterior end 160 adjacent the aperture 168, and a notch 174 formed in the exterior end 160 at an end 176 of the short groove 172. The structure and function of the structural member 130 will be described in greater detail hereinafter.

Figure 10:
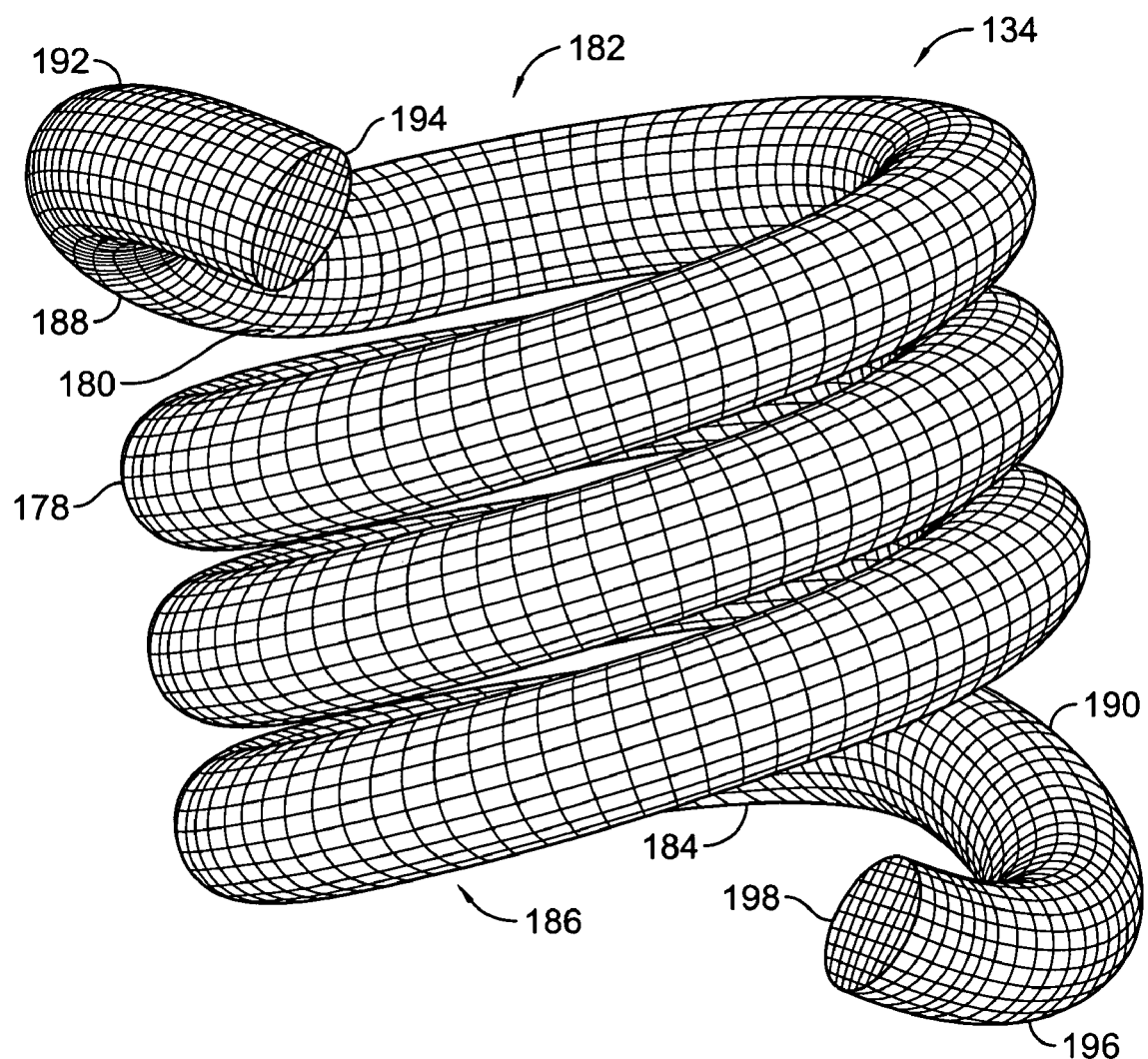
FIG. 10 is a side view of a resilient element that may be employed in forming one or more spring junctions according to the present disclosure.

Referring now to FIG. 10, the outer resilient element 134 consists of coils 178 sharing a common diameter and arranged sequentially about a common axis between a coil termination 180 at an end 182 of the outer resilient element 134 and a coil termination 184 at another end 186 thereof opposite the end 182. Extending from the coil termination 180, and substantially continuous therewith, is a bend region 188 of the outer resilient element 134. Extending from the coil termination 184, and substantially continuous therewith, is a bend region 190 of the outer resilient element 134.

The bend regions 188, 190 of the outer resilient element 134 extend peripherally from the respective coil terminations 180, 184 along respective paths which, when viewed axially (see, e.g., FIG. 13) from either end 182, 186 of the outer resilient element 134, are defined by respective single radii that extend from the common axis of the coils 178 of the outer resilient element 134 and that have extents approximately half that of the common diameter of the coils 178. As a result, the bend regions 188, 190 of the outer resilient element 134 remain within the same peripheral outline defined by the coils 178 of the outer resilient element 134. When viewed from the side, however, as in FIG. 10, the bend regions 188, 190 of the outer resilient element 134 are seen to depart from the helical path defined by the coils 178.

More particularly, the bend region 188, when viewed from the side as in FIG. 10, is seen to include a curve or bend in the path of extension of the bend region 188, according to which the material of the outer resilient element 134: (1) initially curves away from the adjacent coil 178 at the coil termination 180; (2) reaches an apex 192 representing a point of maximum departure from the adjacent coil 178; (3) curves therefrom back toward the adjacent coil 178; and (4) terminates at a bend region termination 194 without fully returning to the helical path defined by the coils 178. Also, the bend region 190, when viewed from the side as in FIG. 10, is seen to include a curve or bend in the path of extension of the bend region 190, according to which the material of the outer resilient element 134: (1) initially curves away from the adjacent coil 178 at the coil termination 184; (2) reaches an apex 196 representing a point of maximum departure from the adjacent coil 178; (3) curves therefrom back toward the adjacent coil 178; and (4) terminates at a bend region termination 198 without fully returning to the helical path defined by the coils 178. The structure and function of the outer resilient element 134 will be described in greater detail hereinafter.

Figure 11:
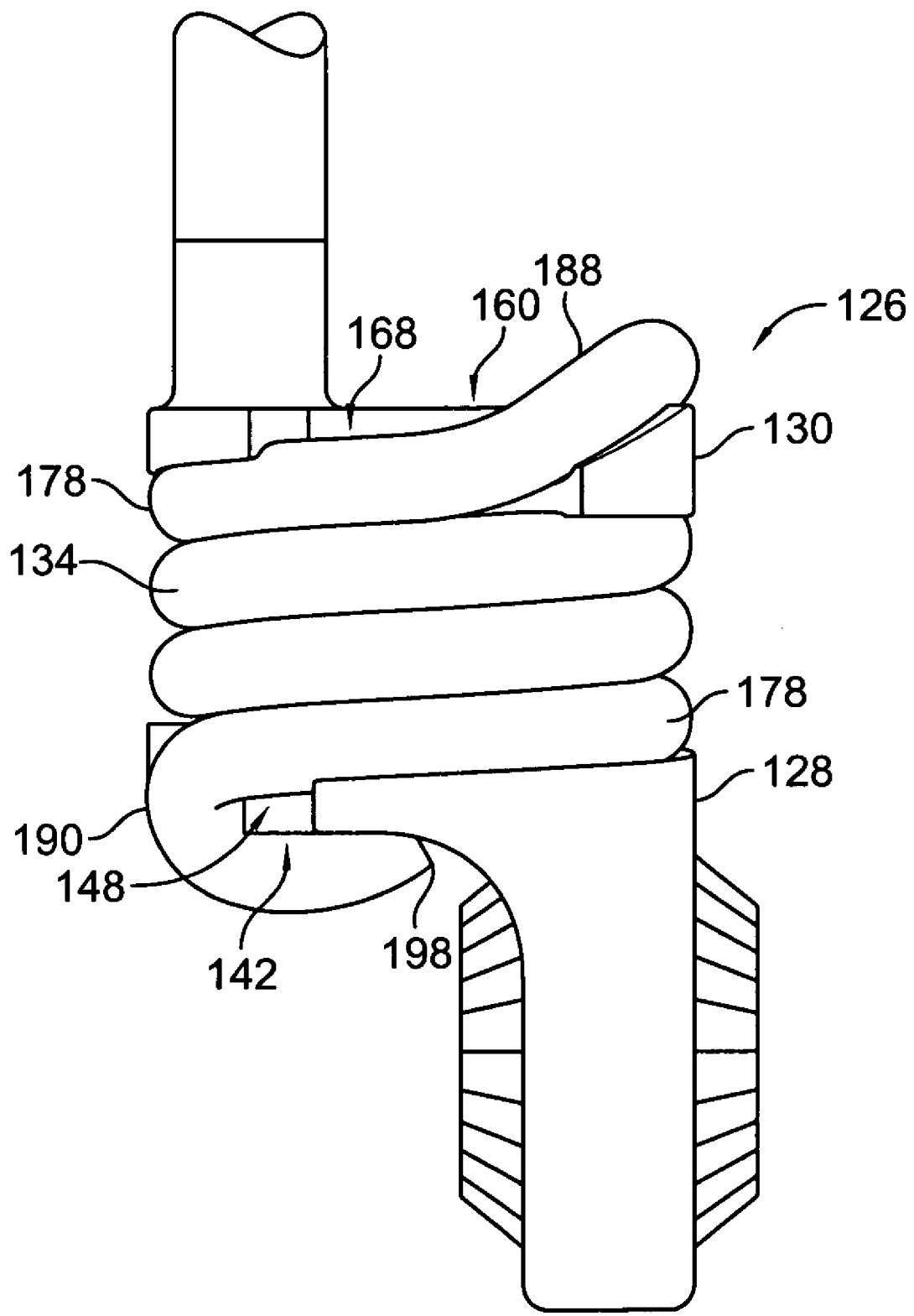
FIG. 11 is a side assembly view of the exemplary spinal stabilization device/system of FIGS. 2-3 illustrating assembly of the components of FIGS. 4-9.

In the assembled state of the dynamic stabilization element 126 shown in FIG. 11, the inner resilient element 132 (obscured, see FIG. 2) is positioned within the outer resilient element 134, between the respective posts 143 (FIG. 4), 162 (FIG. 7), and within the respective annular channels 146 (FIG. 4), 164 (FIG. 7) of the structural elements 128, 130. The bend region 190 and the coil 178 at the end 186 (FIG. 10) of the outer resilient element 134 are threaded into the interior end 140 (FIG. 6) of the structural element 128 until the bend region 190 has substantially passed into or through the aperture 148 of the structural element 128 and the bend region termination 198 has been caused to drop or snap into place within the notch 154 (FIG. 5) formed in the exterior end 142 of the structural element 128. The bend region 188 and the coil 178 at the end 182 (FIG. 10) of the outer resilient element 134 are threaded into the interior end 158 (FIG. 9) of the structural element 130 until the bend region 188 has substantially passed into or through the aperture 168 of the structural element 130 and the bend region termination 194 (obscured, see FIG. 10) has been caused to drop or snap into place within the notch 174 (FIG. 8) formed in the exterior end 160 of the structural element 130.

Figure 12:
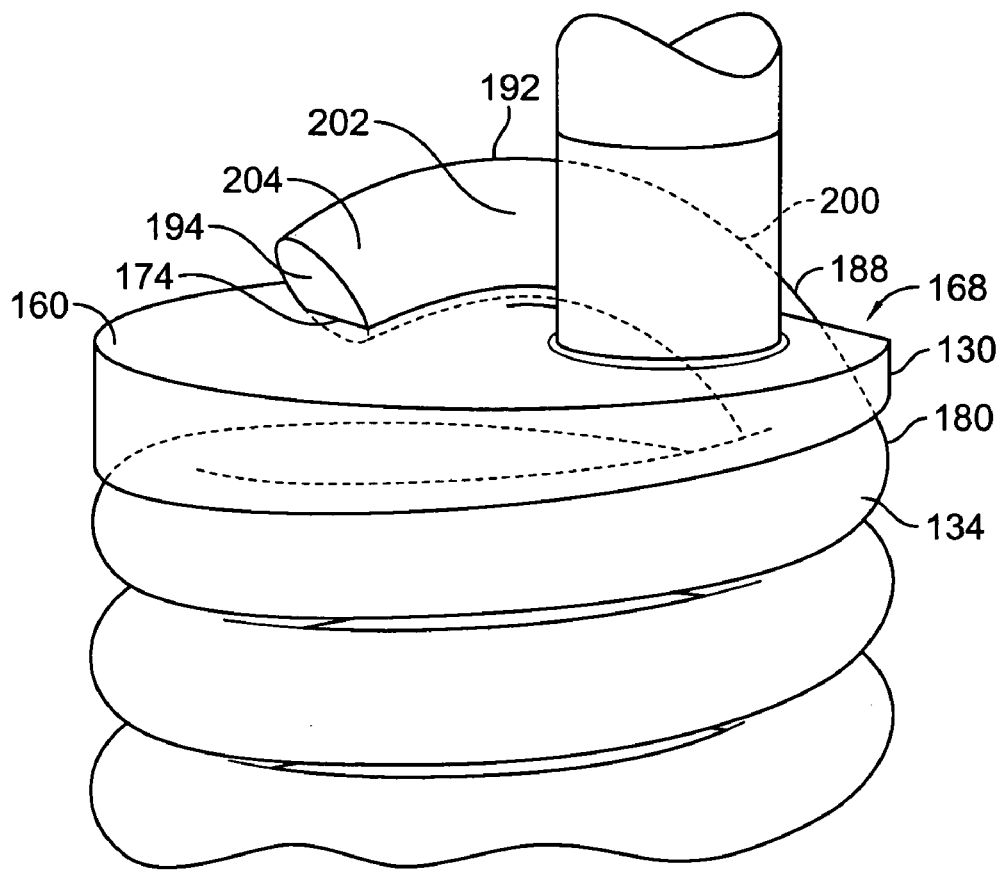
FIG. 12 is a perspective detail view of the interface between the structural member of FIGS. 7-9 and the resilient element of FIG. 10.

Referring now to FIG. 12, the interface or spring junction between the outer resilient element 134 and the structural element 130 is shown in greater detail. As indicated above, the bend region 188 largely or completely extends into or through the aperture 168 formed in the structural element 130, and the bend region termination 194 is lodged within the notch 174 formed in the exterior end 160 of the structural element 130. More particularly, a portion 200 of the bend region 188 of the outer resilient element 134 near the coil termination 180 is lodged within the short groove 172 (FIG. 9) formed in the exterior end 160 of the structural element 130, a portion 202 of the bend region 188 associated with the apex 192 thereof is lodged within the short groove 172 and in longitudinal contact with the exterior end 160 of the structural element 130, and a portion 204 of the bend region 188 associated with the bend region termination 194 is lodged within the short groove 172 to an extent of the notch 174. The short groove 172 formed on the exterior end 160 of the structural element 130 thereby defines a length and an arcuate contour to conform to the arcuate nature of the bend region 188 of the resilient element 134, as explained above in reference to FIG. 10. As shown best by FIGS. 8, 12 and 14, and in reference to the resilient element 134 shown in FIG. 10, the arcuate groove 172 defines a shallow portion to accept the apex 192 of the bend region, and deeper portions on each side of the shallow portion to accept the portion 200 of the bend region 188 near the coil termination 180 and the portion 204 of the bend region 188 associated with the bend region termination 194. In this manner, the depth of the groove 172 varies along its length to accept the bend region 188. The outer resilient element 134 is welded to the exterior end 160 of the structural element 130 in the vicinity of the notch 174, e.g., via electronic-beam welding along an extent of the portion 204 of the bend region 188 that is lodged within the notch 174. The outer resilient element 134 can be placed in a state of full compression in advance of such welding so as to ensure that after such welding, the portion 202 of the bend region 188 associated with the apex 192 thereof is biased in favor of continuous longitudinal contact with the exterior end 160 of the structural element 130 during normal in situ use of, and/or during representative mechanical testing of, the dynamic stabilization element 126.

Though not shown in FIG. 12, a portion (not separately shown) of the bend region 190 (FIG. 10) near the coil termination 184 (FIG. 10) is similarly lodged within the short groove 152 (FIG. 5) formed in the exterior end 142 (FIG. 6) of the structural element 128, a portion (not separately shown) of the bend region 190 (FIG. 10) associated with the apex 196 (FIG. 10) thereof is lodged within the short groove 152 and in longitudinal contact with the exterior end 142 of the structural element 128, and a portion (not separately shown) of the bend region 190 associated with the bend region termination 198 is lodged within the short groove 152 to an extent of the notch 154. The outer resilient element 134 is welded to the exterior end 142 of the structural element 128 in the vicinity of the notch 154, e.g., via electronic-beam welding along an extent of the portion (not separately shown) of the bend region 190 that is lodged within the notch 154 (FIG. 5). The outer resilient element 134 can be placed in a state of full compression in advance of such welding for the same reasons and to achieve a similar biasing effect in the bend region 190 as is described above with reference to the bend region 188.

A cooling/supercooling step may be advantageously undertaken in advance of welding such as is described immediately hereinabove. In accordance with such a step, the outer resilient element 134 and the structural members 128, 130 are immersed in a bath of liquid nitrogen, and are withdrawn therefrom shortly before the resilient element 134 is welded to the structural elements 128, 130. Cooling/supercooling of the outer resilient element 134 and the structural members 128, 130 functions to reduce the likelihood that high levels of heat will be experienced at a distance from the respective weld regions associated therewith. Accordingly, a given heat-affected zone associated with the migration of heat generated by electronic beam welding can be shrunken and/or reduced in extent, as can any soft or weak spot in such heat-affected zone associated with sharply reduced Rockwell hardness. This cooling/supercooling step was observed to increase resilient element durability during representative mechanical testing.

Figure 13:
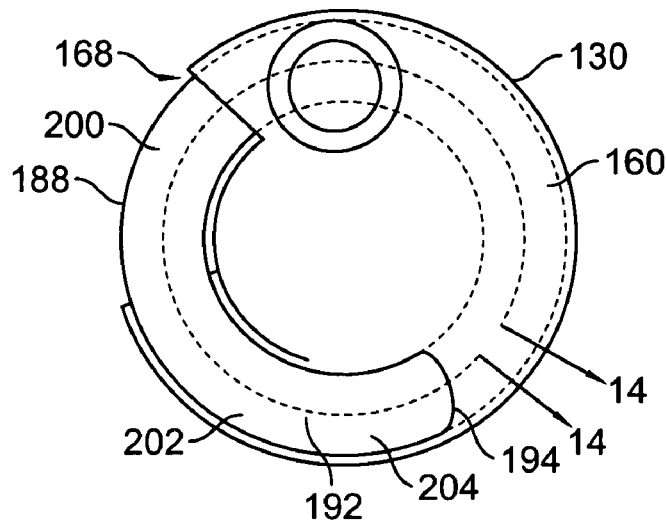
FIG. 13 is a top view of the interface between the structural member of FIGS. 7-9 and the resilient element of FIG. 10.
Figure 14:
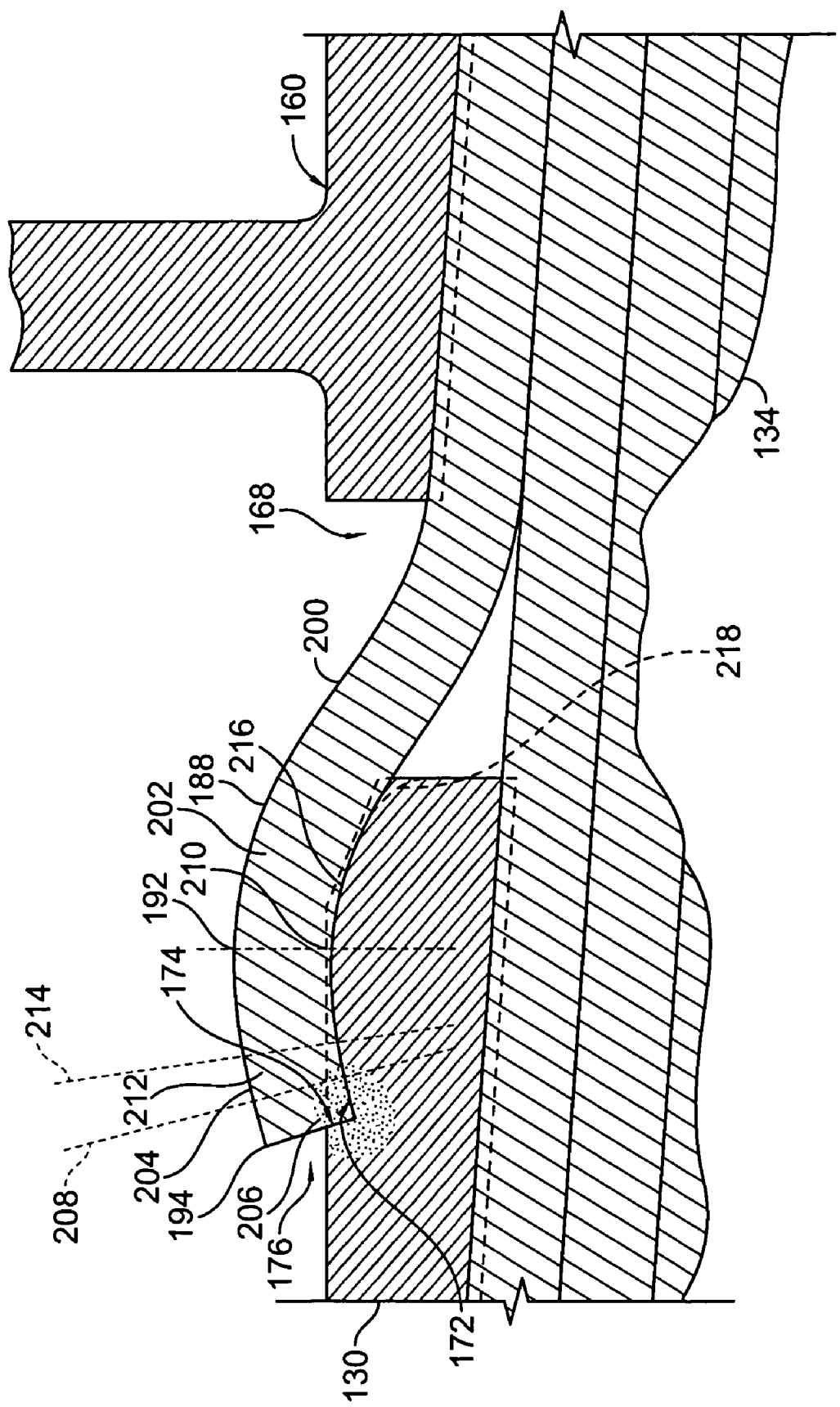
FIG. 14 is a sectional view of the interface between the structural member of FIGS. 7-9 and the resilient element of FIG. 10 taken along the line 14-14 of FIG. 13.

Referring to FIGS. 13 and 14, the above-described welding process produces a weld region 206 incorporating portions of the exterior end 160 of the structural element 130 at the end 176 of the short groove 172 in the vicinity of the notch 174, as well as portions of the bend termination 194 of the bend region 188 of the outer resilient element 134. The portion 204 of the bend region 188 is long enough, and the corresponding portion of the short groove 172 is long enough, such that weld region 206 terminates at a point 208 along the extent of the bend region 188 well short of the apex 192 thereof. Accordingly, the weld region 206 also terminates well short of a corresponding apex 210 of the short groove 172 against which the portion 202 of the zone 212 associated with the process used to affix the outer resilient element 134 to the structural element 130, such region 212 also terminates at a point 214 along the extent of the bend region 188 well short of the apex 192 thereof, as well as well short of the apex 210 of the short groove 172. The portion 202 of the bend region 188 and the exterior end 160 of the structural member 130 are in intimate and continuous longitudinal contact along the short groove 172 at least from the apex 210 thereof and for an extent 216 extending toward the aperture 168. Beyond the extent 216, the short groove 172 tends to depart from intimate contact from the portion 200 of the bend region 188 for an extent 218 extending fully to the aperture 168. The significance and functional benefits of such structure and/or such assembly arrangement between the bend region 188 of the outer resilient element 134 and the exterior end 160 of the structural element 130 will be explained more fully hereinafter.

Figure 16:
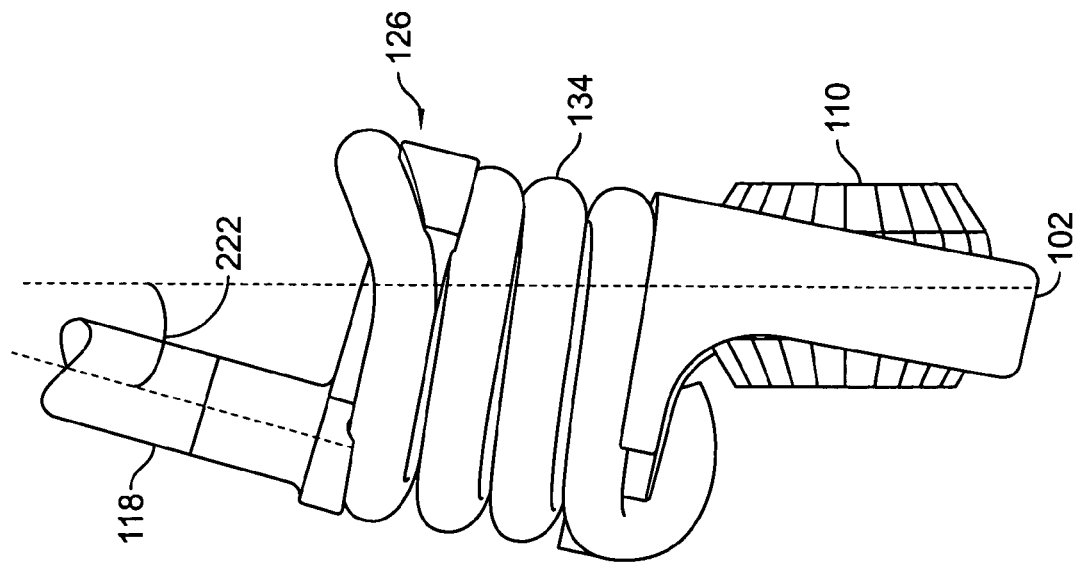
FIGS. 15 and 16 illustrate various exemplary types and ranges of motion associated with exemplary spinal stabilization devices/assemblies of the present disclosure.
Figure 15:
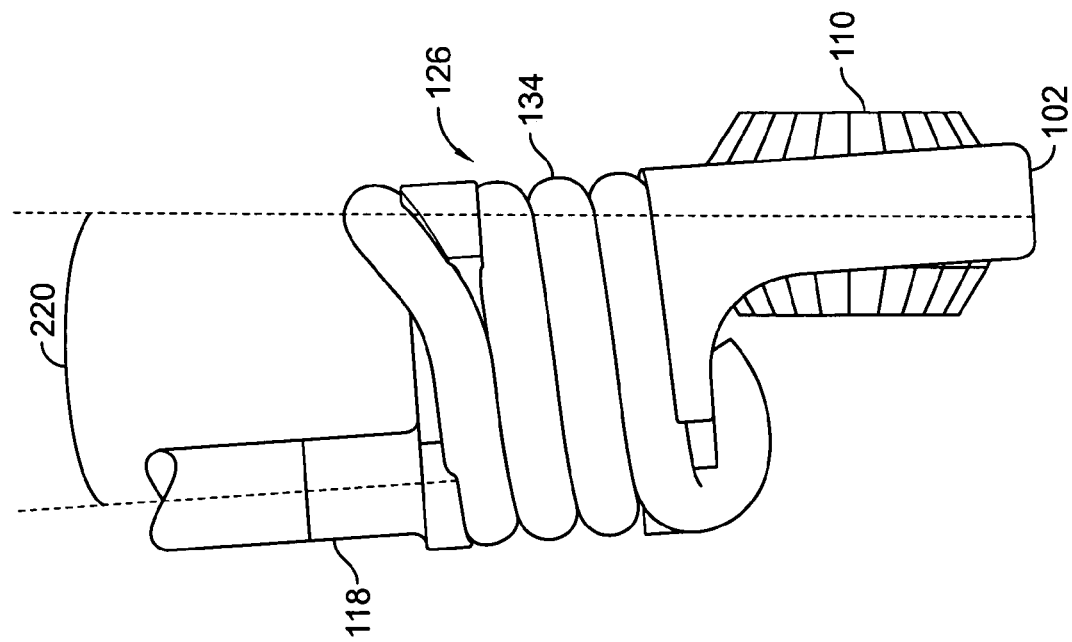

Turning now to FIGS. 15 and 16, in operation, the dynamic stabilization element 126 of the spinal stabilization system 100 (FIG. 2) permits relative rotational motion, as well as relative translational motion, as between the rod 118 and the attachment member 102, and/or as between the rod 118 and the ball/spherical element 110, while providing enhanced spinal support for the patient, e.g., in the "neutral zone" described more fully in the '270 Application. More particularly, the dynamic stabilization element 126 as a unit, and/or the outer resilient element 134 by itself, supports either and/or both of spinal extension and spinal flexion. Referring to FIG. 15, the dynamic stabilization element 126 is shown as it would appear while supporting spinal extension, wherein an extent 220 of, for example, less than 5° of relative rotation as between the rod 118 and the ball/spherical element 110 is produced. Such spinal extension can also produce approximately one millimeter of travel in the resilient element 134 relative to the initial position thereof (i.e., wherein the resilient element 134 is preloaded in tension so as to be slightly extended), such that the resilient element 134 may now actually assume a fully compressed state. Referring to FIG. 16, the dynamic stabilization element 126 is shown as it would appear while supporting spinal flexion, wherein an extent 222 of, for example, greater than 10° of relative rotation as between the rod 118 and the ball/spherical element 110 is produced. Such spinal flexion can produce approximately one and one-half millimeters of travel (i.e., additional extension) in the resilient element 134 relative to the initial position thereof.

Referring again to FIG. 14, the outer resilient element 134 is shown in a state of full compression against the interior end 158 of the structural element 130. As discussed above, when the outer resilient element 134 is in this condition, the bend region 188 of the outer resilient element 134 is biased toward contact with the exterior end 160 of the structural element 130. To the extent the outer resilient element 134 is caused to expand from its fully compressed state, this bias is not relaxed. Rather, this bias is only reinforced by such torsional and/or bending forces as may tend to urge the portion 200 of the bend region 188 further through the aperture 168 in the direction of the interior end 158. (For example, depending on the particular axial and/or lateral forces imposed upon the outer resilient element 134, the portion 200 of the bend region 188 can tend to bend and/or twist close to/closer to the angled exterior surface associated with the extent 218 of the short groove 172). At the same time, the portion 202 of the bend region 188 remains lodged in the short groove 172, where it remains in intimate contact with the exterior end 160 of structural element 130, and as such is not capable of being deflected any further in the direction of the interior end 158 by such axial and/or lateral forces. Accordingly, such axial and/or lateral forces are prevented from directly acting upon either of the weld region 206 or the heat-affected zone 212 of the outer resilient element 134. More particularly, the consistent, continuous longitudinal contact between the portion 202 of the bend region 188 and the exterior end 160 of the structural element 130 along the short groove 172 thereof acts as a permanent 'fulcrum', beyond which the torsional and/or bending forces arising in the portion 200 of the bend region 188 are not necessarily transmitted as such to the weld region 206 or the heat-affected zone 212, at least not in a form capable of producing fatigue-inducing stress in such region/zone. In other words, the active region of the outer resilient element 134 extends no further toward the weld region 206 or the heat-affected zone 212 than the apex 192 of the bend region 188. Since such regions are physically separated from the apex 192 via corresponding structural features of the outer resilient element 134 and the structural member 130, and/or via the manner in which the same are affixed to each other, such forces as are applied to the weld region 206 and the heat-affected zone 212 during in situ use or representative mechanical testing will have been channeled into a cantilevered arrangement. In accordance with such cantilevered arrangement, a fulcrum (e.g., the extent 216 within the short groove 172) provides the weld region 206 with significant mechanical advantage by which to resist such forces without experiencing undue internal stress.

The dynamic stabilization element 126 associated with the spinal stabilization system 100 described hereinabove with regard to FIGS. 2-14 provides numerous advantages in comparison to other spinal stabilization systems associated therewith. Referring again to FIGS. 11 and 14, and while not necessarily intending to be bound by theory, improved reliability and durability is achieved with the disclosed dynamic stabilization element based at least in part on the fact that the heat-affected zone associated with the process of joining the outer resilient element 134 to the structural elements 128, 130 via welding is physically separated from the active region of the outer resilient element 134, and is therefore isolated from the cyclical stress associated with repeated extension/contraction and/or bending during normal use and/or representative mechanical testing. More particularly, the portion 202 of the bend region 188 of the outer resilient element 134 fully separates the portion 202 of the outer resilient element 134 from the portion 204 thereof at which the outer resilient element 134 is welded to the structural member 130. In like measure, and in a similar fashion, the welded and threaded connection between the outer resilient element 134 and the structural member 128 provides similar advantages. Typically, due to the particular structures and assembly methods described above, the heat -affected zone in exemplary embodiments of the present disclosure is observed to extend axially approximately 005"-0.030" from the weld region along the material of the outer resilient element 134, and the active region of the outer resilient element 134 extends no farther in the direction of the welded interfaces than the respective apexes 192, 196 of the bend regions 188, 190. Since the bend regions 188, 190 are each approximately 0.150 inches in length, the increased reliability/durability found in the dynamic stabilization element of the present disclosure has been shown to be at least partially due to the fact that the active region of the outer resilient element 134 is substantially completely shielded from any material degradation that may result from the assembly step, e.g., via electronic-beam welding. In other words, to the extent the use of E-beam welding reduces the Rockwell hardness of a portion or portions of the outer resilient element 134, such portion or portions are substantially completely shielded from fatigue-producing levels of cyclic stress.

The dynamic stabilization element 126 associated with the spinal stabilization system 100 described hereinabove with regard to FIGS. 2-14 can be the subject of numerous modifications and variations while still exhibiting the above-discussed advantages over other dynamic junctions for spinal stabilization systems. For example, the rod 118 can be repositioned to an axial position with respect to the structural member 130. The bend region termination 194 can be affixed to the structural member 130 by other welding processes than E-beam welding, and/or by one or more non-welding means of attachment, such as by clamping or the use of mechanical fasteners appropriate for use in conjunction with small gage springs, by an adhesive-based process, or via the use of a single mold to form the two components together as a single piece. To the extent such attachment schemes result in respective attachment regions along which the bend region termination 194 is affixed to the structural member, such attachment regions are similarly disposed physically separately relative to the respective active region of the outer resilient element 134s (whether or not heat-affected zones are present), and are thereby similarly shielded from the types and levels of cyclical stress known to produce fatigue failure. The outer resilient element 134 need not necessarily be configured in the manner of a coil spring, but may instead take the form of one or more other types of resilient elements, such as a leaf spring, a torsion spring or bar, etc. Additionally, the outer resilient element 134 may be employed in a dynamic junction that does not also include the inner resilient element 132. Many other variations and/or modifications are possible.

Although the present disclosure has been disclosed with reference to exemplary embodiments and implementations thereof, those skilled in the art will appreciate that the present disclosure is susceptible to various modifications, refinements and/or implementations without departing from the spirit or scope of the present invention. In fact, it is contemplated the disclosed connection structure may be employed in a variety of environments and clinical settings without departing from the spirit or scope of the present invention. Accordingly, while exemplary embodiments of the present disclosure have been shown and described, it will be understood that there is no intent to limit the invention by such disclosure, but rather, the present invention is intended to cover and encompass all modifications and alternate constructions falling within the spirit and scope hereof.

The invention claimed is:

1. A spinal stabilization element comprising:
   (a) a spring cap that defines an interior end and an exterior end that is opposite the interior end, the spring cap cooperating with a structural member that is configured and dimensioned to be mounted with respect a spine attachment fastener; and
   (b) a resilient element defining an active region and an attachment region spaced from said active region,
   wherein said resilient element is positioned with respect to said spring cap such that (i) said attachment region is welded exclusively to said exterior end of said spring cap; (ii) said active region extends from said interior end of said spring cap and is physically spaced from said attachment region; (iii) said spring cap supports said resilient element and defines a physical separation between said attachment region and said active region; and (iv) said spring cap defines an arcuate groove for directly engaging and supporting said resilient element between said attachment region and said active region, wherein the groove extends for a length on the exterior end, and wherein the depth of the groove varies along the length.

2. The spinal stabilization element according to claim 1, wherein said attachment region includes a weld region, and further comprising a heat-affected zone of said resilient element, said heat-affected zone being disposed adjacent said weld region and physically separately with respect to said active region.

3. The spinal stabilization element according to claim 1, wherein said attachment region is welded to said exterior end of said spring cap by an electronic-beam welding process.

4. The spinal stabilization element according to claim 1, wherein said resilient element is a spring.

5. The spinal stabilization element according to claim 4, wherein said spring is a coil spring.

6. The spinal stabilization element according to claim 1, wherein said resilient element includes a bend region disposed adjacent said active region, and wherein said arcuate groove is configured and dimensioned to support said bend region such that during in-situ use, said attachment region does not experience fatigue-producing levels of cyclic stress.

7. The spinal stabilization element according to claim 6, wherein said active region includes a coil adjacent said bend region and extending along a helically-shaped path, and wherein said bend region is configured and dimensioned so as to initially bend away from said helically-shaped path and to subsequently bend back toward said helically-shaped path.

8. The spinal stabilization element according to claim 7, wherein said helically-shaped path defines an overall axial direction along which said active region extends in a vicinity of said coil, and said bend region is configured and dimensioned such that said initial bend away from said helically-shaped path is a bend at least partially in said overall axial direction of extension of said active region.

9. The spinal stabilization element according to claim 8, wherein said helically-shaped path defines an axis corresponding to said overall axial direction of extension of said active region, and said bend region is further configured and dimensioned such that said initial bend away from said helically-shaped path does not include a substantial radial component with respect to said axis.

10. The spinal stabilization element according to claim 8, wherein said bend region is further configured and dimensioned so as to remain substantially peripherally aligned with said helically-shaped path when viewed along said axial direction of extension of said active region.

11. The spinal stabilization element according to claim 1, wherein said structural member is mountable with respect to an upwardly extending structure of a pedicle screw.

12. The spinal stabilization element according to claim 1, further comprising a second structural member, said resilient element being operatively coupled to said second structural member.

13. The spinal stabilization element according to claim 1, wherein said active region defines an axial direction of extension toward said spring cap, wherein said resilient element further includes a bend region adjacent said active region and extending still further from said active region along said axial direction of extension to and including an apex in said bend region, and wherein said arcuate groove forms a fulcrum disposed substantially directly beneath said apex for directly engaging and supporting said bend region.

14. The spinal stabilization element according to claim 13, wherein said apex defines a furthest extent of said resilient element along said axial direction of extension.

15. The spinal stabilization element according to claim 13, wherein said fulcrum and said apex are substantially aligned with each other along said axial direction of extension.

16. The spinal stabilization element according to claim 13, wherein said fulcrum is disposed between said apex and said active region of said resilient element along said axial direction of extension.

17. The spinal stabilization element according to claim 1, wherein said active region includes a coil defining an axial direction of extension toward said spring cap, wherein said resilient element further includes a bend region adjacent said active region and extending still further therefrom along said axial direction of extension to and including an apex in said bend region, and wherein said apex defines a furthest extent of said resilient element along said axial direction of extension.

18. The spinal stabilization element according to claim 1, wherein the arcuate groove defines a first deep portion, a shallow portion, and a second deep portion, and wherein the arcuate groove extends from the first deep portion to the shallow portion, and from the shallow portion to the second deep portion 19. The spinal stabilization element according to claim 1, wherein the first deep portion, the shallow portion and the second deep portion define the arcuate groove.

* * * * *